US00PP32392P2

(12) United States Plant Patent
De Wit et al.

(10) Patent No.: US PP32,392 P2
(45) Date of Patent: Oct. 27, 2020

(54) APPLE TREE NAMED 'IPADOR'

(50) Latin Name: ***Malus domestica* Borkh.**
Varietal Denomination: IPADOR

(71) Applicant: BETTER3FRUIT, N.V., Heverlee (BE)

(72) Inventors: Inge De Wit, Lovenjoel (BE); Annemarie Auwerkerken, Beauvechain (BE)

(73) Assignee: BETTER3FRUIT, N.V., Heverlee (BE)

( * ) Notice: Subject to any disclaimer, the term of this patent is extended or adjusted under 35 U.S.C. 154(b) by 0 days.

(21) Appl. No.: 16/602,431

(22) Filed: Oct. 4, 2019

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 5/0875
See application file for complete search history.

(56) References Cited

PUBLICATIONS

PLUTO UPOVROM Plant Variety Database Citation for 'IPADOR' as per QZ PBR 20183058; Nov. 23, 2018; 1 page.*

* cited by examiner

*Primary Examiner* — Kent L Bell
(74) *Attorney, Agent, or Firm* — Foley & Lardner LLP

(57) ABSTRACT

A new and distinct variety of *Malus domestica* apple tree named 'IPADOR', particularly characterized by an extreme long storability and shelf life, scab resistance, very good overcolor development and a strong aroma after storage.

9 Drawing Sheets

Figure 1:
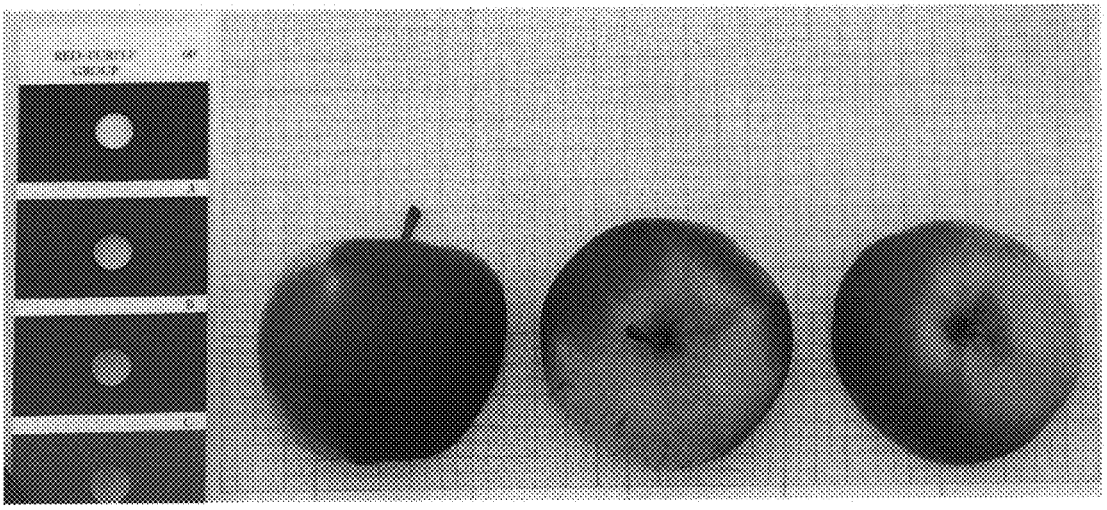

Latin name of the genus and species of the plant claimed: *Malus domestica* Borkh.

Variety denomination: 'IPADOR'.

BACKGROUND OF THE INVENTION

The present invention relates to a new and distinct variety of Apple tree, botanically known as *Malus domestica* Borkh. of the Rosaceae family, and hereinafter referred to by the variety denomination 'IPADOR'.

The new *Malus* variety is a product of a controlled breeding program conducted by the inventors, Inge De Wit and Annemarie Auwerkerken, in Rillaar, Belgium. The objective of the breeding program was to develop a new *Malus* variety with high storability, scab resistance and good flavor.

The new *Malus* variety originated from a cross made by the inventors in 2002 in Belgium. The female or seed parent is the *Malus domestica* variety designated 'GOLDRUSH' (unpatented). The male or pollen parent is the *Malus domestica* variety designated 'NICOTER' (patented; U.S. Plant Pat. No. 17,201, Plant Breeder's Rights Nos. AR 2559, AU 3505, AZ 00134, BR 20090130, BY 251, CA 5381, CH 05.1839, CL 09/08, CN CNA20070569.5, EU 15369, ID 01/Pnrm/TT/08, IL 2957, JP 27353, KZ 94, MD 41, MX 0594, NZ 2988, PH 10-12/35-0078, RS 4,05, RU 4176, SA 2, TR 2009/006, UA 09192, UY 350, VN 82.VN.2011 and ZA 20094207). The new *Malus* variety was discovered and selected by the inventors within the progeny of the stated cross in a controlled environment after the harvest of 2008 in Rillaar, Belgium. Additional selection and asexual reproduction by the inventors occurred after the harvest of 2011 in Rillaar, Belgium.

Asexual reproduction of the new *Malus* variety by grafting onto rootstocks was first performed in the winter of 2008-2009 in Belgium, and has demonstrated that the combination of characteristics as herein disclosed for the new variety are firmly fixed and retained through successive generations of asexual reproduction. The new variety reproduces true to type.

BRIEF DESCRIPTION OF THE INVENTION

The following traits have been repeatedly observed and are determined to be unique characteristics of 'IPADOR' which in combination distinguish this Apple tree as a new and distinct variety:

1. extreme long storability, no Ultra Low Oxygen (ULO) required
2. extreme long shelf life
3. scab resistant (monogenic Vf)
4. very good overcolor development
5. strong aroma after storage In comparison to the parental varieties, 'GOLDRUSH' (unpatented) and 'NICOTER' (patented), 'IPADOR' differs primarily in the traits listed in Table 1.

TABLE 1

| Trait | New Variety 'IPADOR' | Female Parent 'GOLDRUSH' (unpatented) | Male Parent 'NICOTER' (patented) |
|---|---|---|---|
| Fruit: general shape | obloid/conic | oblong/globose | conic |
| Fruit: intensity of over color | dark | low | medium |
| Fruit: relative area of overcolor | large small | absent or very | large to very large |

TABLE 1-continued

| Trait | New Variety 'IPADOR' | Female Parent 'GOLDRUSH' (unpatented) | Male Parent 'NICOTER' (patented) |
|---|---|---|---|
| Fruit: hue of overcolor | dark red | brown red | bright red |
| Fruit: firmness of flesh | very firm | firm | firm |
| Time of eating maturity | very late | very late | late to very late |
| Scab resistance | monogenic Vf | monogenic Vf | none |
| Fruit: sweet/sour balance | sweet/sour | light sweet/sour to very sour | light sweet/sour |
| Storability | extremely long | long | long |

Of the many commercial varieties known to the present inventors, the most similar in comparison to the new *Malus* variety 'IPADOR' is the *Malus* variety 'NICOTER' (patented), in the characteristics described in Table 1.

BRIEF DESCRIPTION OF THE PHOTOGRAPHS

The accompanying photographs illustrate the overall appearance of the new *Malus* variety 'IPADOR' showing the colors as true as is reasonably possible with colored reproductions of this type. Colors in the photographs may differ slightly from the color values cited in the detailed botanical description, which accurately describe the color of 'IPADOR'.

FIG. 1—shows a close-up view (side, top and bottom) of mature fruit of 'IPADOR'.

Figure 2:
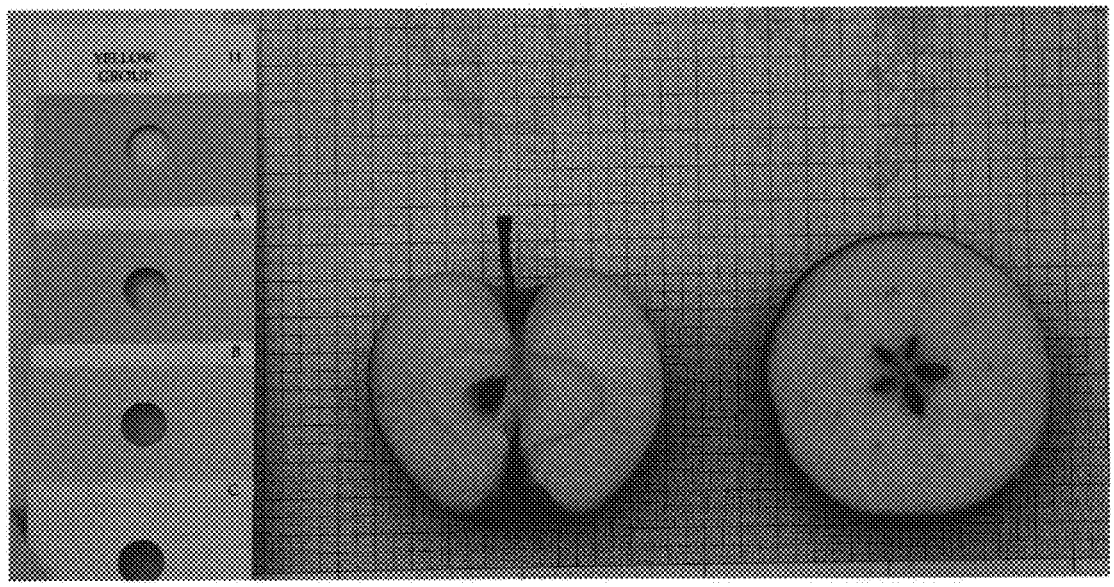

FIG. 2—shows dissection views of mature fruit of 'IPADOR'.

Figure 3:
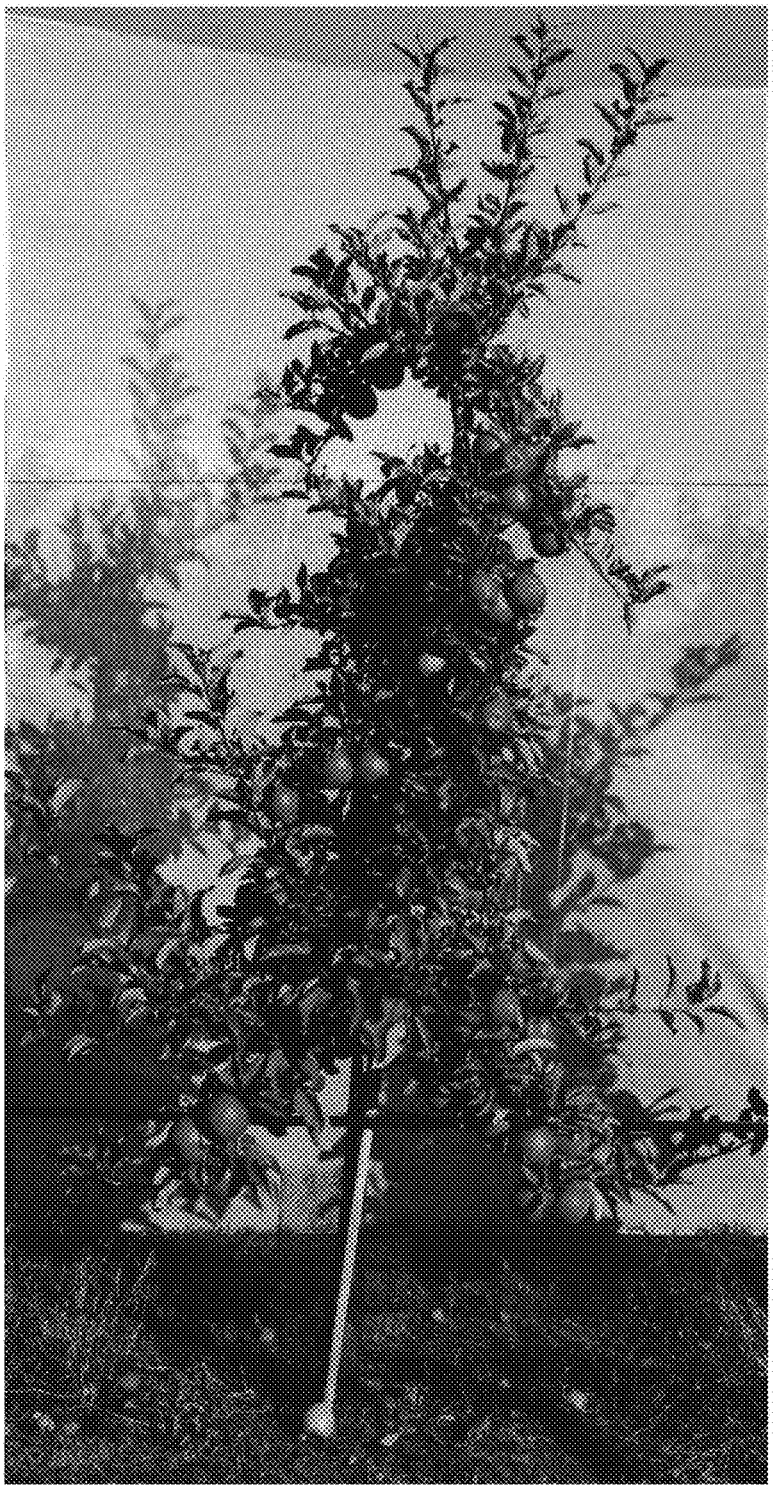

FIG. 3—shows a fruit-bearing tree of 'IPADOR', at 7 years of age.

Figure 4:
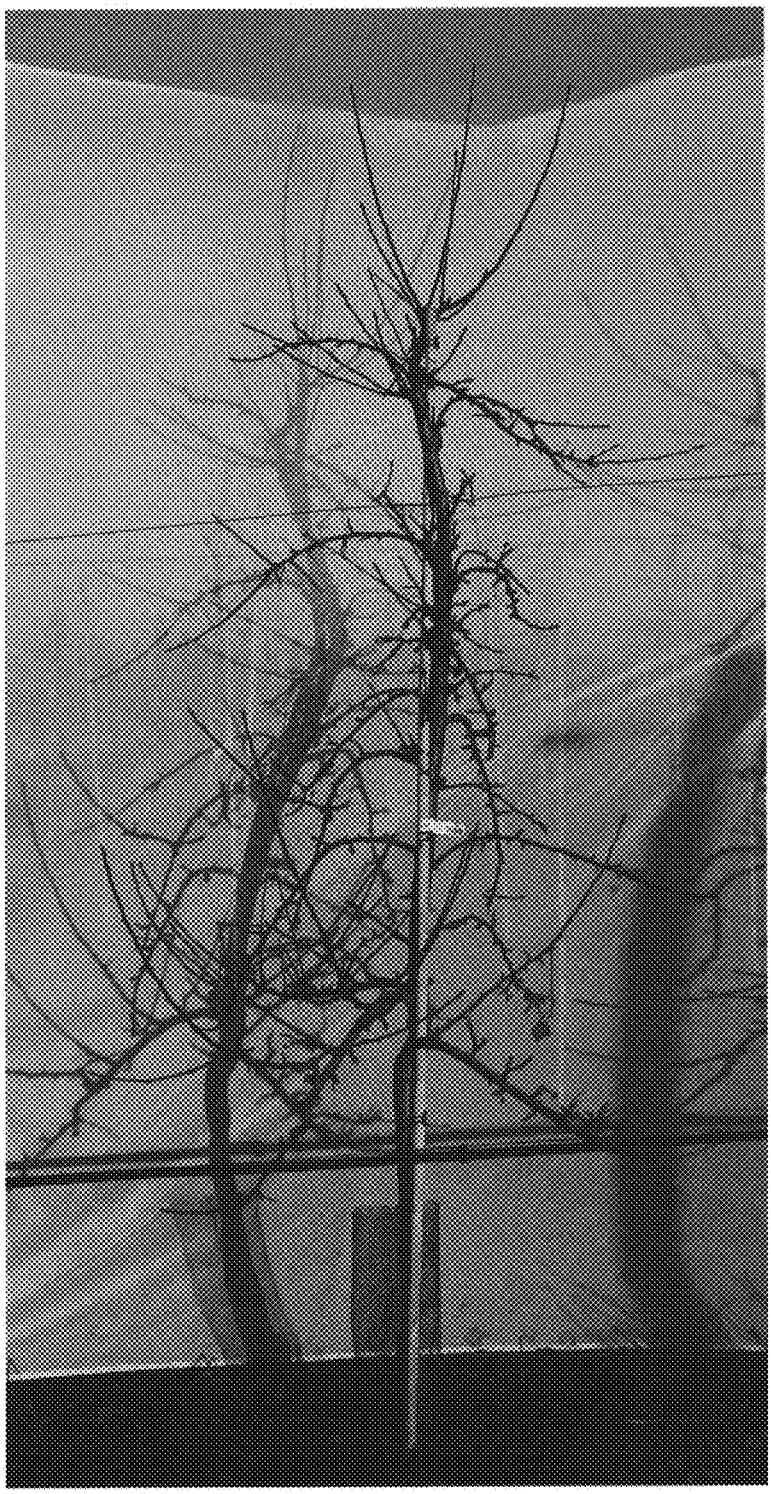

FIG. 4—shows a dormant tree of 'IPADOR', at 7 years of age

Figure 5:
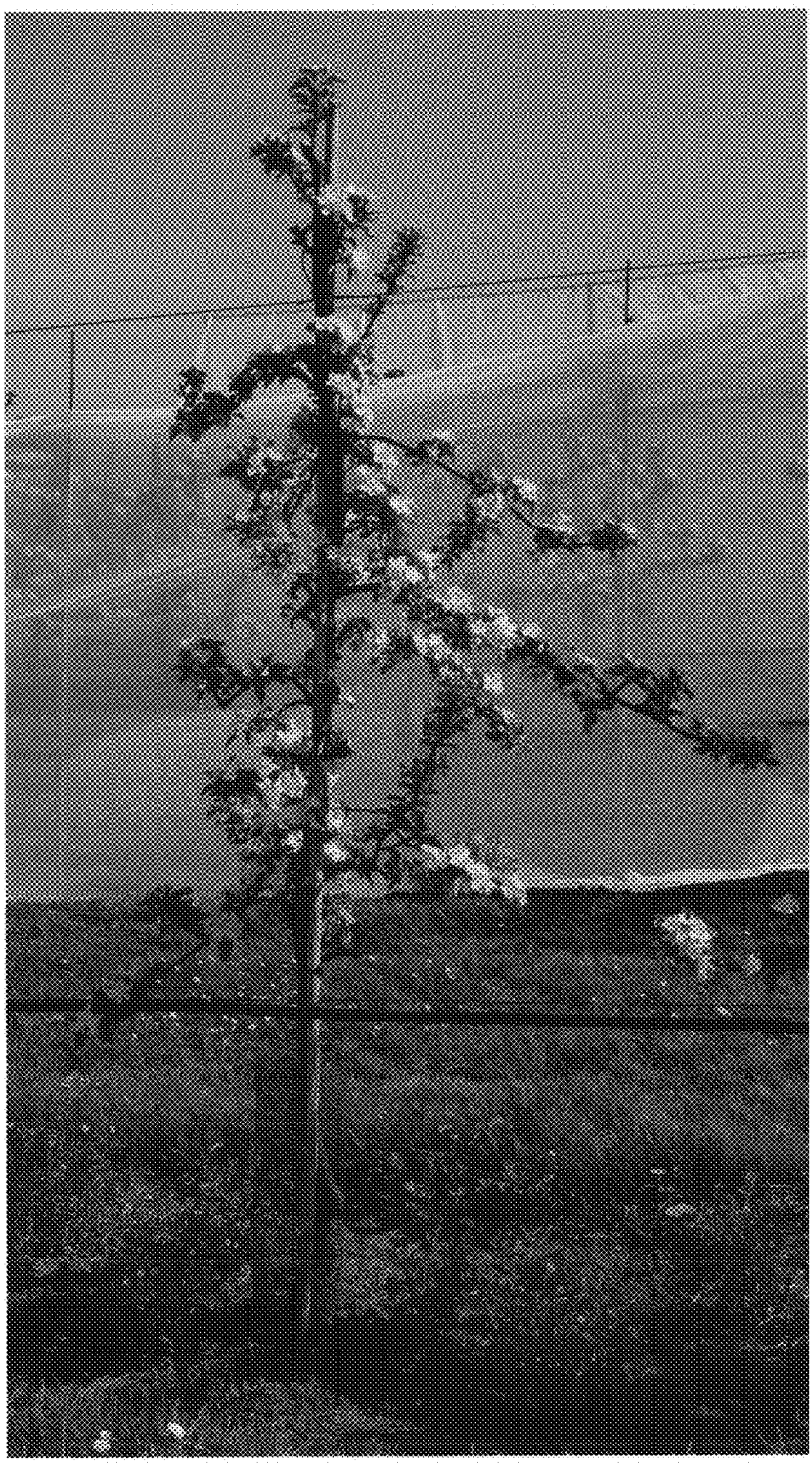

FIG. 5—shows a blooming tree of 'IPADOR', at 7 years of age.

Figure 6:
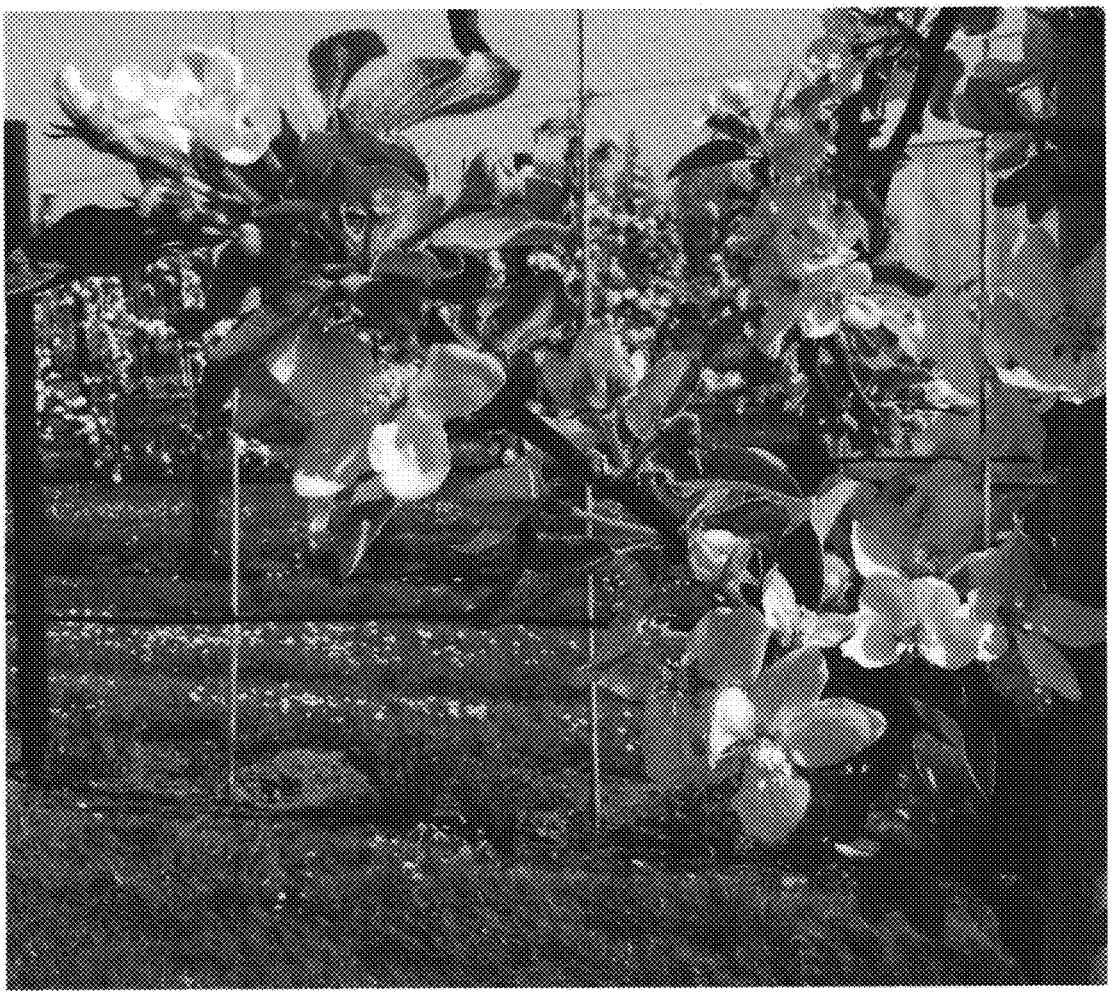

FIG. 6—shows inflorescence of 'IPADOR'.

Figure 7:
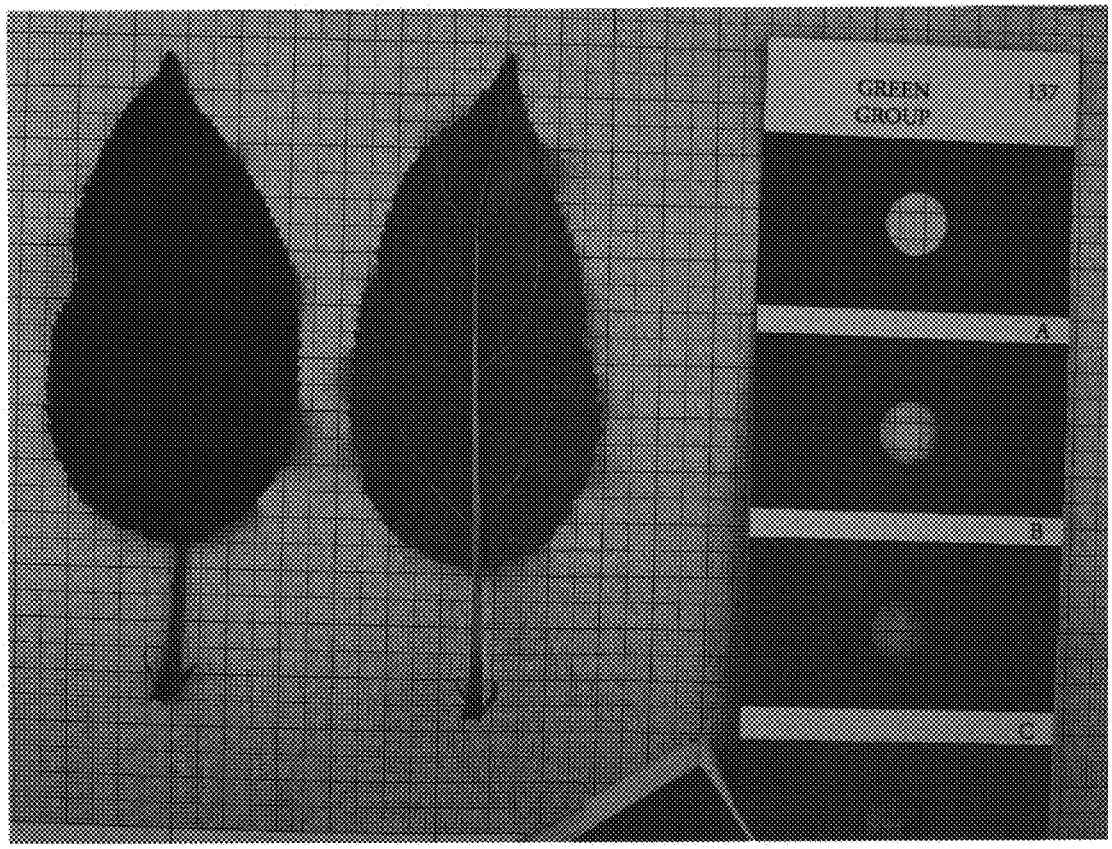

FIG. 7—shows the upper surface (left) and under surface (right) of leaves of 'IPADOR'.

Figure 8:
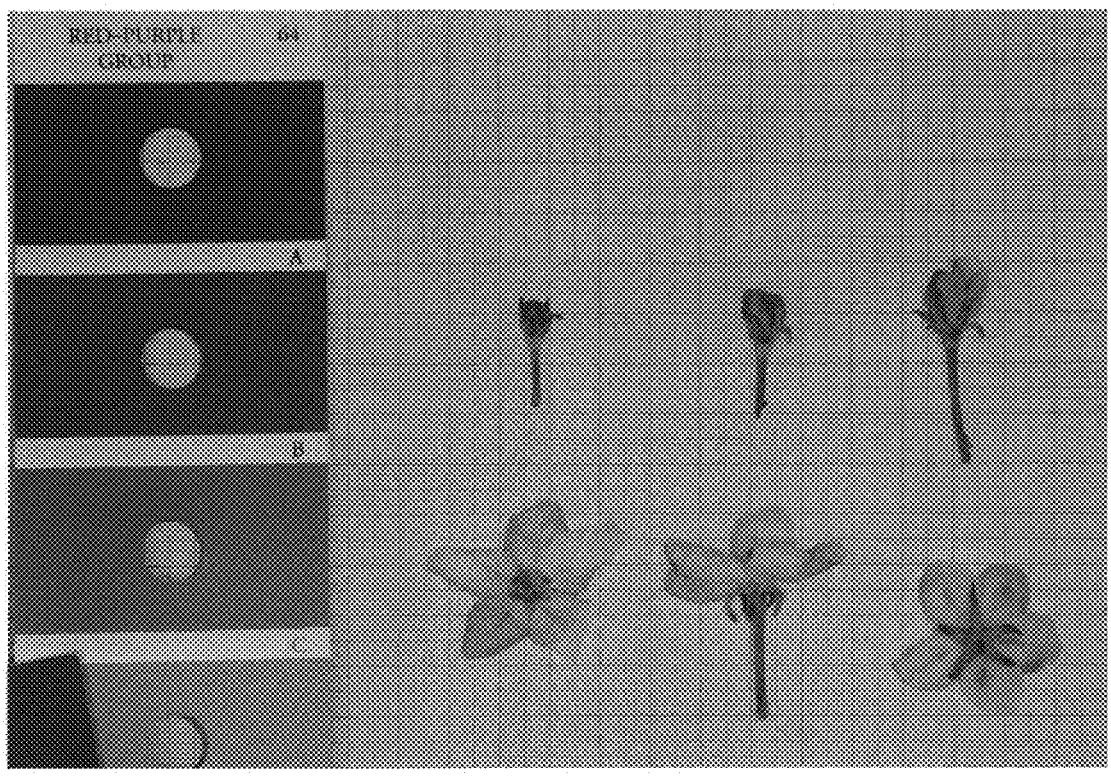

FIG. 8—shows different stages of development of the flowers and (from left to right) the top, side and bottom view of a fully expanded flower of 'IPADOR'.

Figure 9:
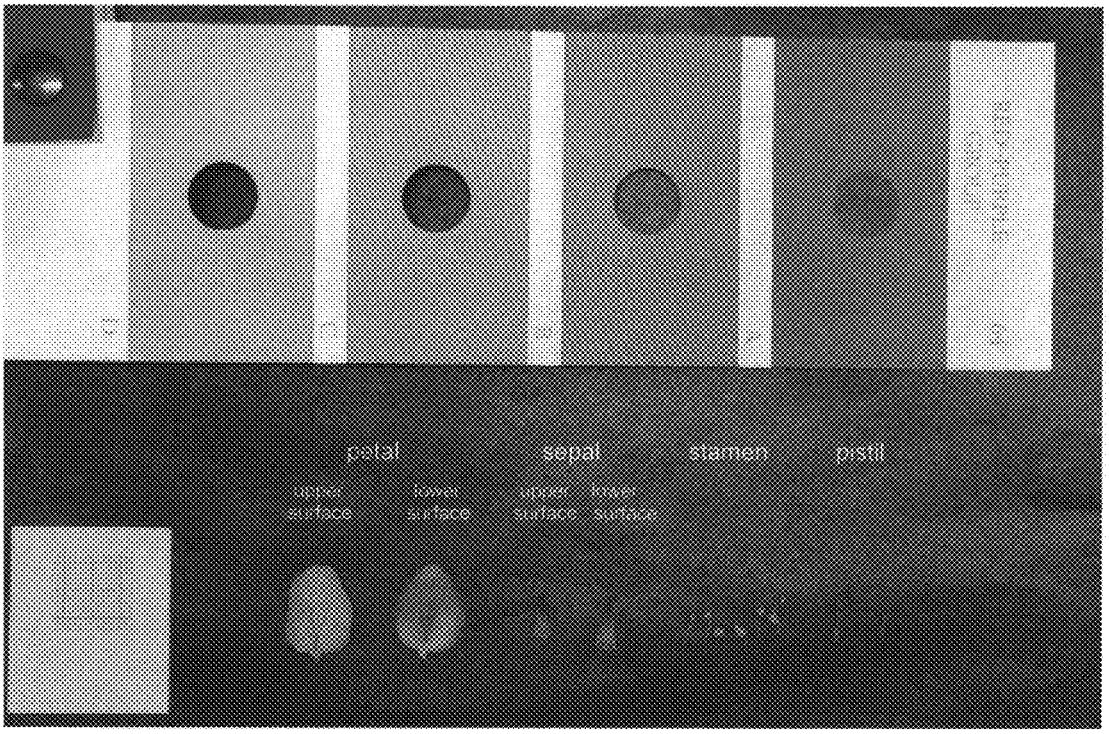

FIG. 9—shows different parts of a flower of 'IPADOR' (from left to right: upper and lower surface of petal, upper and lower surface of sepal, stamen, pistil).

DETAILED BOTANICAL DESCRIPTION

The new *Malus* variety 'IPADOR' has not been observed under all possible environmental conditions. The phenotype of the new variety may vary with variations in environment such as temperature, light intensity, and day length without any change in the genotype of the Apple tree.

The aforementioned photographs, together with the following observations, measurements and values describe trees of 'IPADOR' as grown in Rillaar, Belgium, under conditions which closely approximate those generally used in commercial practice.

Unless otherwise stated, the detailed botanical description includes observations, measurements and values based on 7 year old 'IPADOR' trees grown in Rillaar, Belgium from 2014 to 2019. Quantified measurements are expressed as an average of measurements taken from a number of trees of 'IPADOR'. The measurements of any individual tree, or any group of trees, of the new variety may vary from the stated average.

Color references are made to The Royal Horticultural Society Colour Chart (R.H.S.), ($4^{th}$ edition, 2001), except where general colors of ordinary significance are used. Color values were taken under daylight.

All of the trees of 'IPADOR', insofar as they have been observed, have been identical in all the characteristics described below.

Classification:

*Botanical.*—*Malus domestica* Borkh.

Parentage:

*Female or seed parent.*—*Malus* variety designated 'Goldrush' (unpatented).

*Male or pollen parent.*—*Malus* variety designated 'Nicoter' (patented).

Propagation: Grafting onto rootstocks.

Growing conditions:

*Light intensities.*—Full sunlight or slight shade.

*Temperature.*—During day, grown in range of 2° C. to 23° C., and during evening, grow in range of-5° C. to 13° C. (based on the average month temperature).

Tree:

*Age.*—Observed trees were 7 years old.

*Vigor.*—Medium.

*Form.*—Ramified, spreading.

*Habit.*—A medium-sized tree with one trunk and about 13+/−2 leaders; main branches spreading; crown symmetrical.

*Branching habit.*—Main branches angle is about 67+/−25° with respect to trunk if allowed to grow naturally.

*Density.*—About 2200 trees per hectare.

*Cropping behavior.*—Normal beginning of production, high productivity, no biennial bearing, regular and abundant flowering.

*Type of bearing.*—On spurs only.

*Production.*—High productivity. no biennial bearing.

*Size at maturity.*—Height: About 288+/−34 cm. Spread: About 162+/−13 cm.

*Trunk.*—Height (up to leaders): About 75+/−6 cm. Diameter: About 26+/−3 cm. Texture: slightly rough. Bark color: RHS N200B. Trunk Lenticels: Length: About 3.0+/−0.8 mm. Width: About 1.3+/−0.3 mm. Color: RHS 199B. Density: About 3.5+/−1.3 n° per $cm^2$.

*Branches.*—Number per tree: About 38+/−5. Length: maximum of about 89+/−21 cm; minimum of about 4+/−2 cm. Diameter (at 20 cm from main stem): About 10+/−3 mm. Surface texture: slightly rough. Pubescence: few, white hairs. Color: Mature (after about 3 years old): RHS 177A. New Growth: RHS 166 A. Internode length: About 33+/−11 cm. Internode diameter: About 10+/−4 mm. Branch lenticels: Length: About 2.4+/−0.6 mm. Width: About 1.8+/−0.4 mm. Color: RHS 199B. Density: About 3.9+/−1.6 n° per $cm^2$.

*Spur.*—Present: Yes. Distance between each spur: On the 2 and 3 year old branches, the distance is 3+/−1 cm. Diameter of each spur: About 4+/−1 mm. Number of fruit per spur: About 1.6+/−0.7.

Foliage:

*Arrangement*.—Alternate, simple, petiolated.

*Lamina*.—Size: Length: About 85+/−17 mm (fully expanded leaf). Width: About 45+/−6 mm (fully expanded leaf) Length/width ratio: 1.9+/−0.4. Overall Shape: obtuse, petiolated. Base shape: rounded. Apex shape: acute. Margin: biserrate. Texture: Upper surface: smooth. Under surface: smooth, slightly hairy. Attitude in relation to shoot: upwards. Color (mature leaves): Upper surface: RHS 137A. Under surface: RHS 138B. Color (immature leaves): Upper surface: RHS 143B. Under surface: RHS 143B.

*Venation*.—Type: pinnate. Color: RHS 138B.

*Petiole*.—Length: About 29+/−6 mm. Diameter: About 1.6+/−0.2 mm. Texture: smooth, somewhat hairy (white). Color: RHS 144C, upper and lower surface; RHS 59C at the petiole base; RHS 59D lower surface extending to central vein.

*Stipule*.—Arrangement: free standing. Length (distance of stipules from basal attachment of petiole): About 8.2+/−1.8 mm. Width: About 1.5+/−0.5 mm.

Inflorescence:

*Blooming time*.—Early (similar to 'Idared').

*Blooming period*.—About 1 week.

*Fragrance*.—Slight to quite strong.

*Type*.—Corymb.

*Number of flowers per inflorescence*.—About 5.4+/−0.7.

*Inflorescence size*.—Diameter: About 75+/−9 mm. Depth: About 48+/−3 mm.

*Buds*.—Terminal Buds: Number per spur: About 0.8+/−0.4. Shape: a cone with a circular base. Length: About 10.5+/−2.0 mm. Width: About 5+/−1 mm. Texture: smooth, high pubescence (white; overall but even more at apex). Color: Apex RHS 178A, and base RHS 183A. Scales: Number: About 4.3+/−0.9. Overall shape: triangular, shaped around bud. Apex shape: acuminate or 3 sharp points (middle one highest). Base shape: straight, fully grown together at base. Color: Upper: RHS 178A. Lower: RHS 183A. Lateral Buds: Number per spur: About 2.6+/−1.2. Shape: a cone with an ellipsoidal base. Length: About 7.0+/−2.7 mm. Width: About 3.5+/−0.5 mm. Texture: smooth, light pubescence (white, mostly at apex). Color: Apex RHS 180A, and base RHS 178A. Scales: Number: About 4.6+/−0.6. Overall shape: triangular, shaped around bud. Apex shape: acuminate or 3 sharp points (middle one highest). Base shape: straight, fully grown together at base. Color: Upper: RHS 178A. Lower: RHS 180A.

*Petals*.—Arrangement: intermediate. Number per flower: 5. Size: Length: About 20+/−3 mm. Width: About 15+/−2 mm. Length/width ratio: 1.3+/−0.1. Overall shape: ovoid. Apex shape: obtuse. Base shape: obtuse. Texture (upper surface): smooth with hairs. Texture (lower surface): smooth. Margin: entire. Color (upper surface): RHS 64C and 69D (apex and base). Color (lower surface): RHS 64C and 69D (apex and base).

*Sepals*.—Number per flower: 5. Size: Length: About 8.1+/−1.2 mm. Width: About 4.2+/−0.4 mm. Length/width ratio: 2.0+/−0.3. Overall shape: triangular ending in a sharp point. Apex shape: aristate. Base shape: truncate. Texture (upper surface): smooth, very hairy. Texture (lower surface): smooth, very hairy. Margin: entire. Color (upper surface): Apex RHS 178A, and base RHS 143C. Color (lower surface): Apex RHS 178A, and base RHS 143C.

*Pedicel*.—Length: About 26+/−4 mm. Diameter: About 1.6+/−0.1 mm. Texture smooth, hairy. Color: RHS 143C.

Fruit:

*Keeping quality*.—It can be stored in cold temperature conditions for at least 7 months (normal atmosphere). It has a shelf life of at least 6 weeks.

*Maturity when described*.—After about 2 weeks in storage.

*Maturity period after full bloom*.—About 6 months after full bloom.

*Date of first and last picking* (*harvest*).—$4^{th}$ week of October.

*Type*.—Pome.

*General shape*.—Obloid/conic.

*Average weight*.—About 239+/−41 g.

*Fruit size*.—Average height: About 68+/−5 mm. Average diameter (at widest point): About 80+/−5 mm. Position of maximum diameter: middle. Height/thickness ratio: 0.8+/−0.1.

*Stem*.—Length: About 24+/−8 mm. Diameter: About 2.7+/−0.6 mm. Color: RHS 151C and N163D.

*Stalk cavity*.—Depth: About 15.8+/−2.6 mm. Width: About 38.8+/−2.4 mm.

*Eye basin*.—Depth: About 6.1+/−1.4 mm. Width: About 30.2+/−2.9 mm. Crowning at calyx end: moderate to strong. Position of sepals: Half-closed. Calyx tube: partly open.

*Skin*.—Thickness: About 0.6+/−0.1 mm. Texture: tough. Bloom: absent. Greasiness: absent. Firmness (at picking time): About 8.9+/−0.9 kg/cm$^2$. Overcolor color: RHS 60A. Percentage of skin surface with overcolor color: About 75%. Pattern of overcolor: only solid flush. Intensity of overcolor: high intensity, medium bright. Ground color: RHS 151C. Skin Lenticels: Length: About 1.2+/−0.2 mm. Width: About 1.1+/−0.1 mm. Color: RHS 152C on ground color, RHS 153C on overcolor. Density: About 3.0+/−1.7 n° per cm$^2$.

*Flesh*.—Color: RHS 11C. Texture: very firm, crisp and juicy. Aroma: moderate to strong. Eating quality: well-balanced sour/sweet. Sugar content (at picking time): About 16.1+/−1.3 Brix. Acidity/Starch (at picking time) About 8.2+/−1.3 g/l malic acid. Core: Symmetry of core: round. Distinctness of core lines: weak or not even visible. Locules: Number (per fruit): About 5.1+/−0.2. Length: About 10+/−1 mm. Width: About 5+/−1 mm. Form: teardrop shape.

Seeds:

*Number per fruit*.—About 6.5+/−2.0.

*Number per locule*.—About 1.2+/−0.5.

*Shape*.—Teardrop shape.

*Length*.—About 8.8+/−0.6 mm.

*Width*.—About 5.3+/−0.4 mm.

*Texture*.—Smooth.

*Color*.—RHS 183A.

Reproductive organs:

*Androecium*.—Stamen: Number per flower: About 17.8+/−1.7. Length: About 7.4+/−1.3 mm. Anther: Length: About 2.6+/−0.4 mm. Color: RHS 6D. Filaments: Length: About 6.0+/−1.3 mm. Color: RHS 155D. Pollen: Amount: moderate. Color: RHS 5B. Pollination Requirements: cross pollination.

*Gynoecium*.—Pistils: Quantity: 5. Length: About 8.6+/−0.7 mm. Color: RHS 145B. Stigmas: Color: RHS 144A. Ovary: Length: About 2.4+/−0.4 mm. Width: About 1.8+/−0.3 mm. Color: RHS 145B.

Use: Fresh market.

Disease/pest resistance: Resistant to scab (*Venturia inaequalis*, monogenic Vf).

Disease/pest susceptibility: Susceptible to fire blight (*Erwinia amylovora*).

Winter hardiness: Tolerant to temperatures down to −10° C. without observed damage to wood and buds of dormant Apple trees.

Drought/heat tolerance: Tolerant to temperatures up to 40° C., growth is limited by drought periods without irrigation.

Shipping/storage characteristics: Not sensitive to bruising; stores extremely well at normal atmosphere, so no Ultra Low Oxygen (ULO) storage required.

We claim:

1. A new and distinct variety of *Malus domestica* apple tree named 'IPADOR', as illustrated and described herein.

* * * * *